(12) United States Patent
Popadiuk et al.

(10) Patent No.: US 8,267,961 B2
(45) Date of Patent: Sep. 18, 2012

(54) BARBED SUTURE

(75) Inventors: Nicholas M. Popadiuk, Hillsborough, NJ (US); David Lindh, Sr., Flemington, NJ (US); Dominick Egidio, Flanders, NJ (US)

(73) Assignee: Ethicon, Inc., Somerville, NJ (US)

( * ) Notice: Subject to any disclaimer, the term of this patent is extended or adjusted under 35 U.S.C. 154(b) by 1246 days.

(21) Appl. No.: 11/169,868

(22) Filed: Jun. 29, 2005

(65) Prior Publication Data

US 2007/0005109 A1 Jan. 4, 2007

(51) Int. Cl.
*A61B 17/04* (2006.01)

(52) U.S. Cl. ...................................................... 606/228

(58) Field of Classification Search .......... 606/228–232; 256/8; 264/167
See application file for complete search history.

(56) References Cited

U.S. PATENT DOCUMENTS

| | | | |
|---|---|---|---|
| 3,123,077 A | 3/1964 | Alcamo | |
| 3,494,006 A * | 2/1970 | Brumlik | 24/447 |
| 3,700,544 A | 10/1972 | Matsui | |
| 3,716,058 A | 2/1973 | Tanner, Jr. | |
| 3,720,055 A | 3/1973 | De Mestral et al. | |
| 3,833,972 A | 9/1974 | Brumlik | |
| 3,845,641 A | 11/1974 | Waller | |
| 3,981,051 A | 9/1976 | Brumlik | |
| 4,548,202 A | 10/1985 | Duncan | |
| 4,900,605 A | 2/1990 | Thorgersen et al. | |
| 5,269,783 A | 12/1993 | Sander | |
| 5,342,376 A | 8/1994 | Ruff | |
| 5,395,126 A | 3/1995 | Tresslar | |
| 5,931,855 A | 8/1999 | Buncke | |
| 6,241,747 B1 | 6/2001 | Ruff | |
| 6,599,310 B2 | 7/2003 | Leung et al. | |
| 2003/0001407 A1 | 1/2003 | Hoshikawa et al. | |
| 2003/0041426 A1 | 3/2003 | Genova et al. | |
| 2003/0069602 A1 * | 4/2003 | Jacobs et al. | 606/215 |
| 2003/0074023 A1 | 4/2003 | Kaplan et al. | |
| 2004/0060410 A1 * | 4/2004 | Leung et al. | 83/522.14 |
| 2004/0193191 A1 | 9/2004 | Starksen et al. | |

FOREIGN PATENT DOCUMENTS

| | | | |
|---|---|---|---|
| DE | 1810800 | * | 6/1970 |
| GB | 1091282 | | 11/1967 |
| WO | WO 96/06565 A1 | | 3/1996 |
| WO | WO 2004/030705 A | | 4/2004 |

OTHER PUBLICATIONS

Dattilo, P. P. Jr. et al. "Tissue Holding Performance of Knotless Absorbable Sutures", Society for Biomaterials 29th Annual Meeting Transactions (2003) p. 101.

Mc Kenzie, A. R. "An Experimental Multiple Barbed Suture for the Long Flexor Tendons of the Palm and Fingers", The Journal of Bone and Joint Surgery, (1967) vol. 49B, No. 3, pp. 440-447.

Schmid, A. et al., The outspreading anchor cord. A material for arthroscopic suturing of a fresh anterior cruciate ligament rupture.

U.S. Appl. No. 11/169,869, filed Jun. 29, 2005, titled Braided Barbed Suture.

* cited by examiner

Primary Examiner — Katherine Dowe

(57) ABSTRACT

A barbed monofilament and a method for making the same is provided. The barbed monofilament has a substantially triangular primary cross-section defined by a periphery including first, second and third points of said triangle, and further has a plurality of barbs formed therein. Successive barbs are staggered around the periphery of the monofilament, and extend inwardly into the monofilament to a predetermined depth from the first, second and third points respectively.

26 Claims, 2 Drawing Sheets

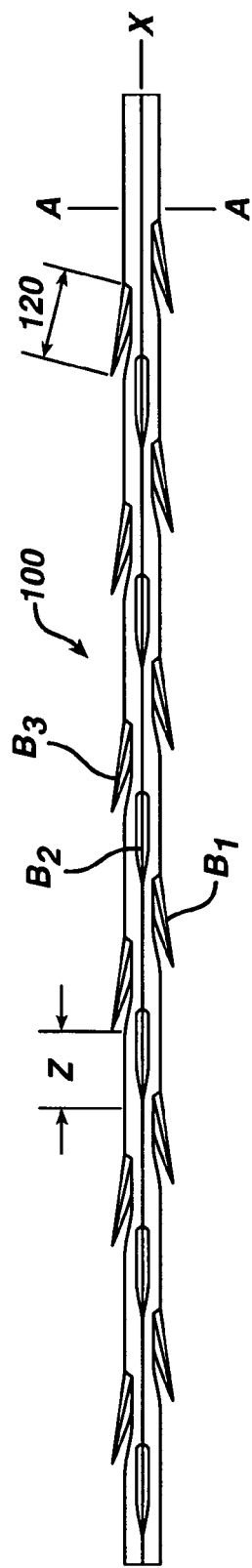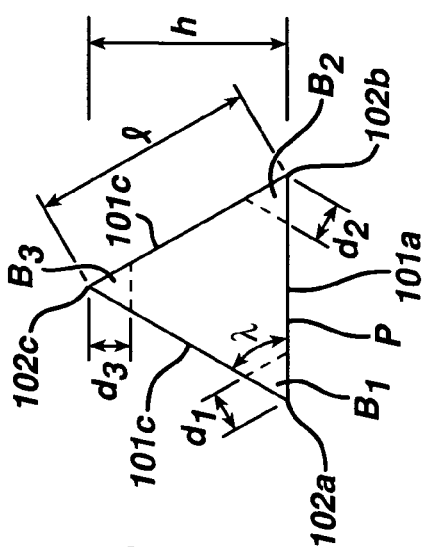

BARBED SUTURE

FIELD OF THE INVENTION

The present invention relates generally to the field of surgical sutures, and more particularly to a barbed surgical suture having a triangular primary cross-section.

BACKGROUND

It is well known that many wounds and surgical incisions are closed using surgical sutures of some sort. Sutures are also commonly used in many other surgical applications, such as to repair damaged or severed muscles, vessels, tissue etc. Typically, the suture is attached at one end to a needle, and the needle is drawn through the tissue to form one or more loops holding the tissue together, and subsequently tied off so that the tissue will remain drawn together. It is also known to incorporate barbs into a monofilament suture in an effort to prevent slippage of the suture within the tissue, an example of which is described in U.S. Pat. No. 5,931,855. U.S. Pat. No. 5,342,376 also describes various embodiments for a barbed tissue connector, one of which is somewhat triangular in overall shape, including the outer periphery of the barbs, rather than having a triangular primary cross-section as will be described further below in relation to the present invention.

Holding strength and tensile strength are primary concerns with any suture, and particularly when barbs are formed in a suture. Since barbed sutures are typically formed by making cuts or slits in the suture using a blade of some type, the slits act as stress concentration points. In applications where a significant load is placed on the suture, i.e., orthopedic applications, a given barb may fail, or begin peeling away from the suture shaft. Once this occurs, due to the fibrous nature of the suture material the barb may be stripped off the suture shaft along a significant length of the suture causing catastrophic failure. Thus, it would be desirable to provide a new and improved monofilament barbed suture having superior holding strength to known barbed monofilament sutures.

SUMMARY OF THE INVENTION

The present invention provides a barbed monofilament having a substantially triangular primary cross-section defined by a periphery including first, second and third points of said triangle, and a plurality of barbs formed therein. Successive barbs are staggered around the periphery of the monofilament, and extend inwardly into the monofilament to a predetermined depth from the first, second and third points respectively. In one embodiment, the primary cross-section is substantially an equilateral triangle, and the barbs are successively staggered at approximately 120 degree intervals. The successive barbs may be formed at a predetermined distance from one another along a length of the monofilament. In one embodiment, the predetermined distance is substantially within the range of 0 to 0.99 inches, and may further be approximately 1/32 of an inch.

In further alternate embodiments, the barbed monofilament may be made of a non-absorbable material selected from the group consisting of polyolefins, polyamides and polyvinylidene fluoride, or of an absorbable material selected from the group consisting of polydioxinone and caprolactone co-glycolide.

In yet further alternate embodiments, the predetermined depth may be within the range of approximately 0.002 to 0.008 inches, and may further be approximately 0.004 inches, or in the case where the substantially triangular primary cross-section is a substantially equilateral triangle having a height, the predetermined depth may be approximately within the range of 15-65 percent of the height.

In yet another embodiment, the length of each barb is within the range of approximately 0.02 to 0.08 inches, and may further be approximately 0.04 inches.

In another embodiment of the barbed monofilament, a distal portion of each barb is defined by a cut extending at an angle of approximately 15 degrees relative to the longitudinal axis of the monofilament, and may further include a proximal portion of each barb defined by a cut extending at an angle of approximately zero degrees relative to the longitudinal axis of the monofilament.

A method for forming a barbed monofilament is also provided which includes the steps of providing a monofilament having a substantially triangular primary cross-section defined by a periphery including first second and third points of the triangle, and forming a plurality of sets of barbs in the monofilament, where each set includes first, second and third barbs extending inwardly to a predetermined depth from the first second and third points respectively. The first, second and third barbs may be separated by substantially equal predetermined distances along a length of said monofilament.

In another embodiment, the barb forming step further includes, for each barb, cutting the monofilament for a first distance using a cutting element positioned at an angle of approximately 15 degrees relative to the longitudinal axis of the monofilament. The barb forming step may also further include, for each barb, following the angled cutting step, further cutting the monofilament for a predetermined distance at an angle of approximately 0 degrees relative to the longitudinal axis of the monofilament.

In yet another embodiment, the length of each barb is within the range of approximately 0.037 to 0.045 inches, and may further be approximately 0.41 inches.

In alternate embodiments, the predetermined depth may be approximately within the range of 0.002 to 0.008 inches, and may further be 0.004 inches, or in the case where the substantially triangular primary cross-section is a substantially equilateral triangle having a height, the predetermined depth may be approximately 15 to 65 percent of the height.

A barbed monofilament is also provided which includes a substantially triangular primary cross-section defined by a periphery including first, second and third points of said triangle, and a plurality of barbs formed therein including at least first, second and third barbs substantially centered around the first, second and third points respectively. The first, second and third barbs may further be formed at successive predetermined intervals along a length of the monofilament.

These and other objects, features and advantages of the present invention will be apparent from the following detailed description of illustrative embodiments thereof, which is to be read in connection with the accompanying drawings.

BRIEF DESCRIPTION OF THE DRAWINGS

FIG. 1 is a side view illustrating one embodiment of a barbed monofilament in accordance with the present invention;

FIG. 2 is a cross-section of the monofilament of FIG. 1 taken along line A-A.

DETAILED DESCRIPTION

Figure 3:
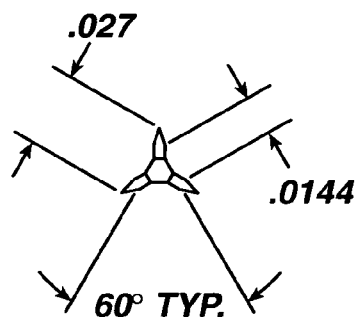
FIG. 3 is an end view of the monofilament of FIG. 1 taken in the direction of the arrow in FIG. 1.

Referring now to FIGS. 1-3, a preferred embodiment of a monofilament barbed suture and the method for forming such a suture will now be described in detail. A side view of a monofilament 100 according to the present invention is illustrated in FIG. 1. An important aspect of the present invention is that the suture described herein is formed from a monofilament having a substantially triangular primary cross-section. This primary cross-section is shown in FIG. 2, and is taken, for example, across line A-A of FIG. 1. By "primary cross-section" what is meant is the shape of the cross section of the monofilament at a location along the length of the monofilament that is not disturbed by the formation of barbs (i.e, does not contain any portion of a barb). "Substantially triangular" is defined so as to include at least all monofilaments with cross-sectional areas that more closely resemble a triangle than they do a circle. In a preferred embodiment, the primary cross-section is a substantially equilateral triangle having a height h and three legs, with each leg 101a, 101b, 101c of the triangle having a length l of approximately 13.5 mils, with an angle x therebetween of approximately 60 degrees.

As will be readily understood following a further description of the manner in which the barbs are formed, the end profile of the monofilament 100 after the barbs are formed will not resemble an equilateral triangle as described above. This is best seen in FIG. 3, which illustrates an end view of the monofilament of FIG. 1 viewed in the direction of the arrow a.

Referring back to FIG. 2, the barbed monofilament device 100 of the present invention is formed by creating barbs in the substantially triangular primary cross-section at each of the three points 102a, 102b, 102c of the triangle, with the depths d1, d2, d3 to which the barbs are cut being indicated generally by the dotted lines of FIG. 4. Although sharp points are illustrated in FIG. 2, it is to be understood that the term "points" is used generally simply to describe the intersection between successive legs of the triangle, which may also be rounded. The barbs may be formed by any suitable, well known method, including by simply using a cutting blade or element such as a razor blade. For an equilateral triangle, the barbs are preferably cut to a depth of approximately 15 to 65% of the height h of the triangle.

For the monofilament described above, the barbs are preferably cut to a 0.004 inch depth (d1, d2, d3) with the blade contacting the monofilament at an angle of approximately 15 degrees relative to the axis X-X of the monofilament. The cut then extends substantially parallel to the axis of the monofilament (i.e., approximately 0 degrees) until the length 120 of the barb is approximately within the range of 0.037 to 0.045 inches, and ideally 0.041 inches. Further, the barbs are preferably staggered at approximately 120 degree increments around the periphery P of the monofilament. In other words, the first barb B1 is by cutting into the first corner of the triangular periphery, the second barb B2 formed by cutting into the second corner, and the third barb B3 formed by cutting into the third corner, with this pattern being subsequently repeated for a second set of three barbs and so on.

Preferably, successive barbs are formed at a spacing z along the length of the monofilament of approximately 1/32 of an inch from one another so that they are staggered both around the periphery of the monofilament and along its length.

The barbed monofilaments described above may be formed of any suitable material, such as any biocompatible absorbable or non-absorbable materials. For example, suitable absorbable materials include classes of materials with glass transition temperatures below room temperature, and semi-crystalline material which include polymers such as polydioxinone (PDS), caprolactone co-glycolide etc., and suitable non-absorbable materials including polyolefins and polyamides. Further, although a triangular primary cross-section that is straight relative to the longitudinal axis is described above, the present invention may also encompass a triangular primary cross-section that is helical relative to the longitudinal axis. This may be accomplished by twisting the monofilament with approximately a quarter of a turn per inch as it comes out of the extruder and is then quenched to hold the monofilament in a twisted type of structure.

The barbed monofilament described above provides significant improvement in holding strength over a barbed monofilament having a circular primary cross-section, but otherwise formed with barbs successively staggered at the same intervals (120 degrees) around the periphery of the monofilament and having substantially identical spacing along the axis of the monofilament. To demonstrate this, comparative testing was done to determine tensile and holding strengths of a barbed monofilament having a triangular primary cross-section with barbs formed therein as described above, and barbed monofilaments having a circular primary cross-sections with barbs formed therein in a substantially identical manner. Comparisons were made with respective monofilaments having substantially identical masses (a monofilament with a triangular primary cross section having a mass corresponding to that of a standard size 2.0 suture having a circular primary cross-section), and with respective monofilaments having substantially identical starting tensile strengths before having barbs formed therein (with the monofilament having the triangular primary cross-section having less mass).

In a first test a standard 2.0 polyvinylidene fluoride (PVDF) suture having a circular primary cross-section had an initial tensile strength of 11.33 lbs., which was reduced to 2.56 lbs. after forming barbs therein in the manner described above (0.004 depth at an angle of 15 degrees). A suture formed of the same material and having the same mass, but having a triangular primary cross-section, however, had an initial holding strength of 12.05 lbs., which was reduced to 6.25 lbs. after forming barbs therein in the same manner. Thus, the suture having a circular primary cross-section had a 77% reduction in tensile strength whereas the suture having a triangular primary cross-section had only a 48% reduction in tensile strength. For a second test, a suture having a triangular primary cross-section and a substantially identical initial tensile strength of 11.22 lbs. (and therefore less mass), showed a reduction in tensile strength to 5.65 lbs. (45%) after forming barbs therein.

With regard to the initial comparison of sutures having substantially identical masses, the barbed suture having a triangular primary cross-section also had substantially improved holding strengths as compared to the barbed suture having a circular primary cross-section. Holding strengths were measured by the force required to remove the suture from a foam block, which was approximately 0.48 lbs. for the former and 0.25 lbs. for the latter.

These results demonstrate that a suture having a triangular primary cross-section and barbed as described above have substantially improved tensile strength and holding strength as compared to comparable devices with a circular primary cross-section.

Although illustrative embodiments of the present invention have been described herein with reference to the accompanying drawings, it is to be understood that the invention is not limited to those precise embodiments and that various other changes and modifications may be effected herein by one skilled in the art without departing from the scope or spirit of the invention.

What is claimed is:

1. A barbed monofilament comprising a triangular primary cross-section defined by a periphery including first, second and third points of said triangle, and a plurality of barbs formed therein, wherein successive barbs are staggered around the periphery of the monofilament, and extend inwardly into the monofilament to a predetermined depth from the first, second and third points respectively, and wherein a distal portion of each barb is defined by a cut extending for a first length at a substantially constant angle relative to a longitudinal axis of the monofilament, and a proximal portion of each barb is defined by a cut extending for a second length at an angle of approximately zero degrees relative to the longitudinal axis of the monofilament,
wherein the barbed monofilament is comprised of a non-absorbable material selected from the group consisting of polyolefins, polyamides and polyvinylidene fluoride, and wherein the barbed monofilament is adapted for use as an implantable surgical suture for approximating tissue.

2. The barbed monofilament according to claim 1, wherein the primary cross-section is substantially an equilateral triangle, and wherein the barbs are successively staggered at approximately 120 degree intervals.

3. The barbed monofilament according to claim 1, wherein successive barbs are formed at a predetermined distance from one another along a length of the monofilament.

4. The barbed monofilament according to claim 3, wherein the predetermined distance is substantially within the range of 0 to 0.99 inches.

5. The barbed monofilament according to claim 4, wherein the predetermined distance is approximately 1/32 of an inch.

6. The barbed monofilament according to claim 1, wherein the predetermined depth is within the range of approximately 0.002 to 0.008 inches.

7. The barbed monofilament according to claim 6, wherein the predetermined depth is approximately 0.004 inches.

8. The barbed monofilament according to claim 1, wherein the triangular primary cross-section is a substantially equilateral triangle having a height, and wherein the predetermined depth is approximately within the range of 15-65 percent of the height.

9. The barbed monofilament according to claim 1, wherein a length of each barb is within the range of approximately 0.02 to 0.08 inches.

10. The barbed monofilament according to claim 9, wherein the length of each barb is approximately 0.04 inches.

11. A barbed monofilament comprising a triangular primary cross-section defined by a periphery including first, second and third points of said triangle, and a plurality of barbs formed therein, wherein successive barbs are staggered around the periphery of the monofilament, and extend inwardly into the monofilament to a predetermined depth from the first, second and third points respectively, and wherein a distal portion of each barb is defined by a cut extending for a first length at a substantially constant angle relative to a longitudinal axis of the monofilament, and a proximal portion of each barb is defined by a cut extending for a second length at an angle of approximately zero degrees relative to the longitudinal axis of the monofilament, wherein the barbed monofilament is comprised of an absorbable material selected from the group consisting of polydioxinone and caprolactone co-glycolide, and wherein the barbed monofilament is adapted for use as an implantable surgical suture for approximating tissue.

12. The barbed monofilament according to claim 11, wherein the primary cross-section is substantially an equilateral triangle, and wherein the barbs are successively staggered at approximately 120 degree intervals.

13. The barbed monofilament according to claim 12, wherein successive barbs are formed at a predetermined distance from one another along a length of the monofilament.

14. The barbed monofilament according to claim 13, wherein the predetermined distance is substantially within the range of 0 to 0.99 inches.

15. The barbed monofilament according to claim 14, wherein the predetermined distance is approximately 1/32 of an inch.

16. The barbed monofilament according to claim 11, wherein the predetermined depth is within the range of approximately 0.002 to 0.008 inches.

17. The barbed monofilament according to claim 11, wherein the triangular primary cross-section is a substantially equilateral triangle having a height, and wherein the predetermined depth is approximately within the range of 15-65 percent of the height.

18. The barbed monofilament according to claim 17, wherein a length of each barb is within the range of approximately 0.02 to 0.08 inches.

19. A method for forming a barbed monofilament comprising the steps of:
forming a monofilament having a triangular primary cross-section defined by a periphery including first second and third points of the triangle, wherein the barbed monofilament is comprised of a non-absorbable material selected from the group consisting of polyolefins, polyamides and polyvinylidene fluoride, or an absorbable material selected from the group consisting of polydioxinone and caprolactone co-glycolide; and
forming a plurality of sets of barbs in said monofilament, wherein each set includes first, second and third barbs extending inwardly to a predetermined depth from the first second and third points respectively, and wherein the barb forming step further comprises, for each barb, cutting the monofilament for a first distance using a cutting element positioned at a substantially constant angle relative to a longitudinal axis of the monofilament and subsequently further cutting the monofilament for a predetermined second distance at an angle of approximately 0 degrees relative to the longitudinal axis of the monofilament,
wherein the formed barbed monofilament is adapted for use as an implantable surgical suture for approximating tissue.

20. The method according to claim 19, wherein the first, second and third barbs are also separated by substantially equal predetermined distances along a length of said monofilament.

21. The method according to claim 19, wherein the barb forming step further comprises, for each barb, cutting the barbed monofilament for the first distance using a cutting element positioned at an angle of approximately 15 degrees relative to the longitudinal axis of the monofilament.

22. The method according to claim 21, wherein a length of each of said barbs is within the range of approximately 0.037 to 0.045 inches.

23. The method according to claim 22, wherein the length of each of said barbs is approximately 0.041 inches.

24. The method according to claim 22, wherein the predetermined depth is approximately within the range of 0.002 to 0.008 inches.

25. The method according to claim 24, wherein the predetermined depth is approximately 0.004 inches.

26. The method according to claim 22, wherein the triangular primary cross-section is a substantially equilateral triangle having a height, and wherein the predetermined depth is approximately 15 to 65 percent of the height.

* * * * *